United States Patent
Murray (10) Patent No.: US 6,210,031 B1
(45) Date of Patent: Apr. 3, 2001

(54) BONE CEMENT DEVICE AND PACKAGE

(76) Inventor: William M. Murray, 2650 Spring Hill La., Enola, PA (US) 17025

(*) Notice: Subject to any disclaimer, the term of this patent is extended or adjusted under 35 U.S.C. 154(b) by 0 days.

(21) Appl. No.: 09/506,202

(22) Filed: Feb. 16, 2000

Related U.S. Application Data (62) Division of application No. 09/235,591, filed on Jan. 22, 1999.

(51) Int. Cl.[7] .................. B01F 13/06; B01F 9/10
(52) U.S. Cl. .............. 366/139; 366/194; 366/197; 366/241; 366/219
(58) Field of Search .................. 366/139, 189, 366/194, 224, 267, 197, 205, 241, 219

(56) References Cited

U.S. PATENT DOCUMENTS

| | | | |
|---|---|---|---|
| 4,277,184 | * 7/1981 | Solomon | 366/139 |
| 4,808,184 | 2/1989 | Tepic | 604/56 |
| 5,265,956 | 11/1993 | Nelson et al. | 366/139 |
| 5,328,262 | 7/1994 | Lidgren et al. | 366/139 |
| 5,370,221 | 12/1994 | Magnusson et al. | 206/221 |
| 5,398,483 | 3/1995 | Smith et al. | 53/474 |
| 5,505,538 | 4/1996 | Earle | 366/139 |
| 5,549,380 | 8/1996 | Lidgren et al. | 366/139 |
| 5,588,745 | 12/1996 | Tanaka et al. | 366/130 |
| 5,842,785 | * 12/1998 | Brown et al. | 366/139 |
| 5,842,786 | * 12/1998 | Solomon | 366/139 |
| 5,857,771 | * 1/1999 | Draenert | 366/139 |
| 6,042,262 | 3/2000 | Hajianpour | 366/139 |

* cited by examiner

Primary Examiner—Tony G. Soohoo
(74) Attorney, Agent, or Firm—Thomas Hooker, P.C.

(57) ABSTRACT

A device for stirring bone cement includes a bone cement cartridge having a piston at one end of the cartridge and an elongate stirrer extending through the piston and along the cartridge. Bone cement powder and liquid are mixed in the cartridge by relative rotation between the cartridge and stirrer. The mixed bone cement is extruded from the cartridge by moving the piston along the cartridge and the stirrer.

34 Claims, 8 Drawing Sheets

BONE CEMENT DEVICE AND PACKAGE

This application is a division of my co-pending application for Bone Cement Mixer and Method, Ser. No. 09/235,591 filed Jan. 22, 1999.

FIELD OF THE INVENTION

The invention relates to stirring and extruding of orthopedic bone cement to an application site.

DESCRIPTION OF THE PRIOR ART

Cement used as a casting and grouting material to implant prosthetic devices into live bone is made from a very fine cement powder, typically polymethyl methacrylate, mixed with a monomer liquid, typically methyl methacrylate, to form a flowable bone cement mixture. Physical mixing of the dry cement powder and liquid is required in order to make a flowable cement. It is not sufficient to merely bring the liquid into contact with the cement powder because the liquid will not flow into the powder uniformly. During mixing the monomer liquid should be distributed equally throughout the mixture so that the mixture is uniform and possesses a uniform viscosity, consistent with the manufacturer's specifications.

Bone and dental cements are stirred or mixed using pre-packaged amounts or doses of dry bone cement powder and monomer liquid prepared by the manufacturer of the cement. The amounts of powder and liquid are measured to provide a cement mixture having desired properties when the powder and liquid are uniformly mixed together. Failure to mix the liquid and powder together uniformly means that part of the mixture contains an excess of monomer liquid and is runny and part of the mixture contains a deficiency of monomer liquid and is more viscous than desired or, in some cases, retains unwetted dry powder.

Bone cement is conventionally mixed in a closed bone cement mixer. The mixer has a mixing chamber, a cover to close the chamber, and a mixing element or stirrer movable within the mixing chamber to mix the powder bone cement and monomer liquid together physically and form a flowable bone cement. Cement is mixed by placing the required amounts of bone cement powder and monomer liquid in the mixing chamber, which may be the interior of a syringe cartridge seated in the mixer. A cover is placed on the top of the mixer to close the mixing chamber. The cover supports a mixing element or stirrer which is inserted into the cement powder when the cover is placed on the mixing chamber. Vacuum may be applied to the interior of the chamber to withdraw gas. The mixing element is manually rotated in the chamber for a predetermined amount of time to mix the powder and liquid and form a flowable bone cement. Insertion of the stirrer into the bone cement powder before monomer liquid is poured onto the powder compacts the powder and makes uniform mixing difficult.

Prior to mixing, bone cement powder is typically poured into the empty mixing chamber and monomer liquid is poured into the chamber on top of the powder. Alternatively, the monomer liquid may be poured into the mixing chamber before bone cement powder is poured into the chamber. When several doses of bone cement are mixed, powder and monomer liquid may be poured into the mixer alternately. When the dry bone cement powder is poured into the mixing chamber, it forms a body having a height. The body is comprised of loosely compacted particles within the chamber. Before physical mixing of the bone cement the monomer liquid is not uniformly distributed along the height of the powder body. When the liquid is poured on top of the powder, the liquid can form a puddle which seals the top of the powder and prevents underlying air between particles of the bone cement powder from flowing out of the powder. Trapped air can form inclusions in mixed bone cement.

The problems of uneven monomer liquid distribution just described can be quite significant where the height of the body of bone cement powder is greater than its diameter. This is typically the case when the cement is mixed in a tall, narrow bone cement cartridge of the type used to extrude mixed cement to an application site. Because of this problem, some conventional mixers use wide bowl-type mixing chambers rather than narrow cartridges. Cement mixed in a bowl-type mixing chamber must be transferred from the bowl-type chamber to a cartridge for extrusion to a prepared application site. The transfer from the bowl-type mixing chamber to a cartridge takes time, involves loss of cement and, most seriously, includes a likelihood of trapping air inclusions in the body of mixed cement. Air inclusions weaken bone cement.

After the bone cement powder and liquid are poured into the mixing chamber, the ingredients are physically mixed together by moving the stirrer in the mixing chamber. However, when mixing in a bone cement cartridge, it can be difficult to produce uniform distribution of monomer liquid along the height of the body. Where there is excess monomer liquid, the mixed bone cement will be less viscous than the manufacturer's standard. Where there is an excess of powder, the resulting mixture will be more viscous than the standard and, indeed, may contain regions where there is no monomer liquid.

It is quite important that monomer liquid be evenly distributed throughout the bone cement mixture. Bone cement with an excess of monomer liquid sets up slowly requiring increased operating room time and the risk of prosthesis displacement during protracted set-up. Such cement also possesses reduced strength. Further, during the increased set-up period there is a risk that blood or other bodily fluid will displace runny cement from adjacent the formed bone surface at an implant site and thereby weaken fixation between the hardened cement and bone.

Bone cement mixed with a deficiency of monomer liquid has a high viscosity and may be difficult to flow properly to the application site. This cement does not flow readily into the irregularities of a prepared bone surface to form a reliable joint. Further, bone cement with a deficiency of monomer liquid sets up relatively rapidly, reducing the already short amount of time available to the surgeon to perform an implantation procedure.

The implantation of a bone prosthesis using a bone cement mixture in which part of the bone cement has an excess of monomer liquid and is relatively runny and part of the bone cement has a deficiency of monomer liquid and is relatively viscous, causes additional problems in the operating room because the surgeon is not able to predict with accuracy the proper length of time for the cement to set and form a joint securing an implanted prosthetic element to a prepared live bone application site. Setting must occur before any stress may be placed on the prosthetic element. Premature stressing of the implanted element will displace the carefully placed element and will impair fixation. For instance, the initial seating of a prosthetic hip ball in the adjacent hip socket stresses the implanted stem on the ball and must be delayed until the bone cement securing the stem in the proximal end of the femur has set. When bone cement is not mixed uniformly, the surgeon must delay seating the ball in the socket for a period of time greater than the specified time for setting the cement. A surgeon implanting a prosthetic element using the bone cement cannot rely on the set-up time specification provided by the bone cement manufacturer. The specification assumes uniform mixing of the cement.

The problems described above are well recognized. A conventional method for achieving greater uniformity of monomer liquid distribution when using a syringe cylinder as a mixing chamber requires pouring cement powder and monomer liquid alternately, in small amounts, into the chamber until the total amounts to be mixed have been poured into the chamber. The powder and liquid are then mixed. While this method can achieve improved uniformity of monomer liquid distribution, it has serious disadvantages. First, it consumes valuable extra time, and the duration of the time consumed results in a mixture which is not homogeneous in terms of the starting time of its mixing and, hence, its setting time. Second, the layering of monomer liquid which results from this method can isolate regions of loosely packed dry powder containing air which will not be effectively removed by application of vacuum during mixing and will form air inclusions in the mixed cement.

Bone cement may be mixed by pouring bone cement powder from a manufacturer's package into a mixing chamber, either a mixing bowl or a bone cement cartridge. The dry powdered bone cement is compacted in the package. When opened and poured, the very fine particles of the bone cement expand or fluff to increase the volume of the bone cement powder appreciably. Fluffed bone cement powder may occupy one and one half times the volume of settled bone cement powder. Because bone cement powder fluffs when poured it is conventional to use a large funnel to receive the powder and guide the bone cement powder into a mixing chamber and to provide oversized mixing bowls. In pouring the cement powder, it is virtually impossible to avoid generating a cloud of powder dust which settles on nearby instruments and materials. This is a significant problem in mixing bone cement, particularly as the powder is highly abrasive.

In conventional bone cement mixers the mixing element or stirrer is inserted into the mixing chamber after the bone cement powder and monomer liquid have been placed in the chamber. When mixing is complete, the stirrer is withdrawn from the cement. Inevitably, cement will adhere to the stirrer as it is withdrawn and will thereby be wasted. Usually the mixture is sufficiently stiff that stirrer withdrawal leaves air-containing recesses in the cement remaining in the mixer. These recesses can form air inclusions. Stirrer withdrawal from the cement exposes a large surface area of the cement to room air and undesirably introduces significant amounts of monomer liquid vapor in the air. Conventional bone cement mixers cannot be used more than one time and are discarded after one use, resulting in significant expense per use and generation of appreciable wasted cement.

Mixing of bone cement is further complicated because there are two types of commercially available bone cement powder. A first type of bone cement powder is made up of small spherules of bone cement and fine fragments of ground bone cement powder. The fragments are smaller than the spherules and occupy interstices between the spherules. In this type of bone cement powder, referred to as spherule and fragment powder, monomer liquid does not readily penetrate into the powder. For instance, a volume of monomer liquid poured onto the top of one or more doses of spherule and fragment bone cement powder in a cartridge would penetrate a short distance into the powder, wet the fragments adjacent the top of the powder with the remainder of the monomer liquid forming a puddle on the top of the powder.

A second type of bone cement powder includes bone cement spherules only, without fragments in the interstices between spherules. In this type of powder, referred to as spherules only powder, the open interstices between the spherules permit flow of monomer liquid into the powder.

Effective bone cement mixing requires that the mixer be capable of distributing the bone cement liquid throughout the bone cement powder. Specialized mixers may be required, depending upon whether bone cement is to be mixed from a spherule and fragment type powder or from a spherule only type powder.

Thus, there is a need for an improved bone cement mixer and method which distributes monomer liquid uniformly along the height of a body of mixed bone cement. There is also a need for improved placement of bone cement powder in a tall, narrow bone cement mixing chamber, such as a bone cement cartridge, without the necessity of pouring powder into the cartridge prior to mixing. There is also a need for an improved bone cement mixer where mixing is performed without insertion of a stirring element into the bone cement powder before mixing, and without withdrawal of the stirring element after mixing. A reusable bone cement mixer is also needed.

SUMMARY OF THE INVENTION

The invention relates to bone cement mixers, components and methods for mixing very fine bone cement powder, either spherules and fragments powder or spherules only powder, and monomer liquid with the monomer liquid distributed throughout the bone cement so that the mixed cement has essentially uniform viscosity and is free of air inclusions.

The cement is preferably mixed in a high, narrow bone cement cartridge. Preferably this cartridge is supplied to the user already filled with dry compacted bone cement powder, and with a stirrer element inside. The bone cement powder is then evacuated. A high velocity narrow stream of monomer liquid is then flowed down into the top of the bone cement column and penetrates the height of the column. Monomer liquid from the stream impacts the bone cement powder and is absorbed into the powder surrounding the stream, forming a cylinder of monomer-rich powder surrounding the stream. The bone cement powder away from the monomer-rich column remains dry. The monomer liquid in the cylinder is distributed essentially uniformly along the height of the column. After flowing the monomer liquid into the column, the bone cement powder and monomer liquid are mixed to form bone cement having an essentially uniform viscosity. The cartridge is then placed in a conventional bone cement gun for extrusion to an application site.

Mixing of the monomer liquid and bone cement is performed by relative rotation of the cartridge body and un-mixed bone cement and a stirrer in the cartridge. The stirrer may be held against rotation while the cartridge is rotated.

The stirrer may be mounted in the cartridge piston and held stationary with the piston during mixing. When the cartridge is placed in a cement gun, the piston is moved past the stirrer to extrude the uniformly mixed cement with reduced waste. The cement is extruded directly from the cartridge in which it was mixed without air inclusions. Seals on the piston prevent leakage of cement during mixing and extrusion of mixed cement.

Prior to mixing, monomer liquid is poured into a monomer chamber located on top of the mixer and the monomer chamber is immediately covered by a lid. The lid is held closed during flow of the monomer liquid into the bone cement and during mixing. Monomer gases are evacuated from the mixer through the vacuum system used to withdraw air from the mixer. Escape of monomer liquid vapors which occurs during mixing of bone cement in an open bowl or chamber is avoided.

The mixer includes a manual drive for rotating the cartridge relative to the fixed stirrer held in the cartridge. The monomer chamber is located above a disk portion of the drive which engages the top of a collar on the cartridge to rotate the cartridge. An opening is provided in the disk below the nozzle forming the monomer stream. In this way, the monomer liquid passes freely through the opening in the disk and into the evacuated cement powder column in the cartridge. The mixer also includes a valve for automatically releasing monomer liquid when the lid is closed on the top of the monomer well, thereby providing immediate dispensing of monomer liquid into the bone cement powder, simplifying mixing operations and reducing the time required to mix a batch of cement.

The bone cement cartridges used for mixing cement in the disclosed mixer include a cylindrical body, a specialized piston at one end of the body, an extension collar mounted on the other end of the body with a stirrer located inside the cylindrical body and collar and mounted in slots in the piston. An appropriate number of doses of compacted bone cement powder is loaded into the cartridge and sealed in the cartridge at atmospheric pressure by the manufacturer. A seal is adhered to the lip at the top of the collar to confine the dry powder in the cartridge. The seal is preferably formed from a sheet of permeable material which permits the pressure of the air inside the cartridge to adjust to the pressure of the air outside of the cartridge.

The piston carrying the stirrer includes lip seals extending around a two arm stirrer and a lip seal extending around the circumference of the piston engaging the interior of the cylindrical body. These seals prevent leakage of bone cement. A cap is preferably fitted over the end of the body at the piston to protect the piston prior to mixing.

The mixer is reusable and may be used repeatedly to mix batches of bone cement in bone cement cartridges. The cement powder, monomer liquid and mixed cement are at all times confined within a cartridge.

Other objects and features of the invention will become apparent as the description proceeds, especially when taken in conjunction with the accompanying drawings illustrating the invention, of which there are six sheets and one embodiment.

DESCRIPTION OF THE PREFERRED EMBODIMENT

Figure 1:
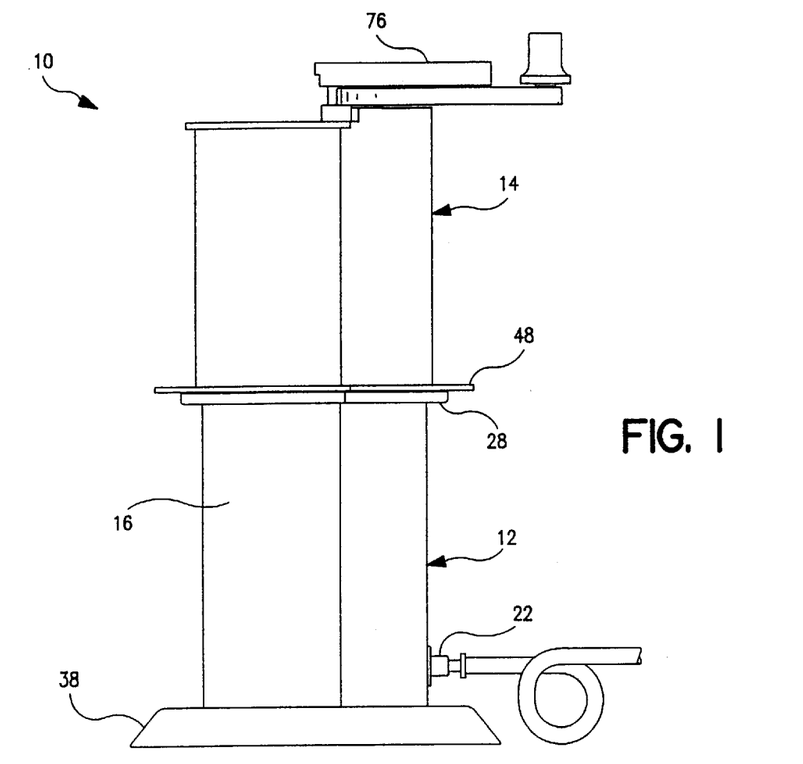
FIG. 1 is a side view of a bone cement mixer.

Bone cement mixer 10 includes a cartridge housing 12 and a cover 14 removably mounted on the top of the housing. The cartridge housing and cover are preferably molded from thermoplastic resin, which may be transparent, although other materials may be used if desired. Cartridge housing 12 includes a cylindrical wall 16 having a closed bottom wall 18. When assembled as shown in FIG. 1, the housing and cover define a body surrounding closed cylindrical mixing chamber 20 above the bottom wall and open at the top of the housing. A vacuum port 22 is located on the side of the housing across from chamber 20 and opens into internal passage 24 extending to the top of the housing and communicating with the chamber. Outer circumferential lip 26 extends around the housing 12 a short distance below the top of the housing. Lip 26 carries an upwardly facing circumferential sealing gasket 28.

Cylindrical cartridge alignment ring 30 extends up from the center of bottom wall 18. Integral alignment key 32 is provided on one side of ring 30. See FIGS. 6 and 9. Circular cartridge support ring 34 extends upwardly from bottom wall 18 a short distance inwardly from wall 16. Four vertical alignment ribs 36 are spaced around the inside of wall 16 and extend from the bottom wall to the top of the chamber. The height of the ribs is reduced adjacent the top of chamber 20 to accommodate and permit rotation of an extension collar described below. Enlarged circumferential base 38 extends around the bottom of housing 12 to facilitate stable positioning of mixer 10 on a support surface.

Cover 14 includes a continuous circumferential vertical wall 40 comprising a pair of partial cylindrical sections 42 and 44. The lower part of wall 40 has a close sliding fit over partial cylindrical wall 16 on one side of housing 12 and the partial cylindrical wall 46 on the other side of the housing. Wide circumferential flange 48 extends around the bottom of wall 40 and engages sealing gasket 28 to form a tight seal between the housing and cover. Flange 48 is wider than lip 26 to facilitate manual mounting of the cover on the housing and ready removal of the cover to open the mixer. The cover closes the top of the mixer to prevent ambient air from flowing into the mixing chamber when the cover is mounted on the housing. In this way, the pressure in the chamber may be reduced by withdrawing air through port 22.

Figure 8:
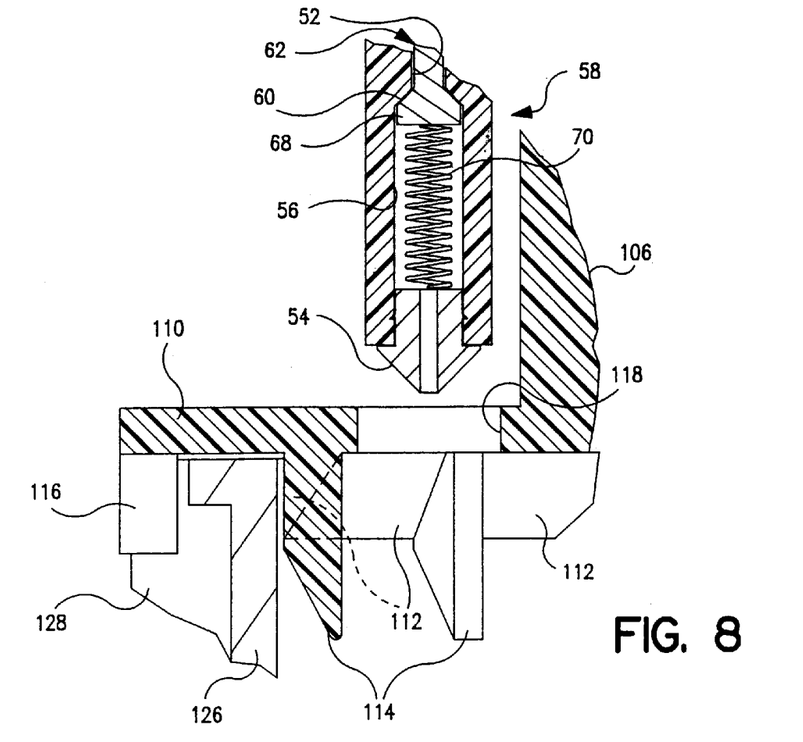
FIG. 8 is an enlarged view of portion A of FIG. 2.

The cover includes a preferably transparent monomer well or chamber 50 located above mixing chamber 20. The monomer well is open on the outside of cover 14. A discharge passage 52 at the bottom of well 50 extends downwardly to nozzle 54. Nozzle 54 is above and aimed down at chamber 20. As shown in FIG. 8, the lower portion 56 of passage 52 is enlarged in diameter to receive the nozzle.

The discharge passage 52 is opened and closed by monomer liquid valve 58 shown in FIG. 8. The valve includes valve seat 60 located at the upper end of portion 56 and an elongate valve member 62 fitted in passage 52 and including an upper rod 64 having an end located a short distance below the top 66 of the monomer well. The diameter of valve rod 64 is less than the diameter of passage 52 to permit flow of monomer liquid down the passage. An expanded valve head 68 on the lower end of rod 64 is normally held against seat 60 by spring 70 located in the enlarged lower portion 56 between the nozzle and the head 68. The upper portion of rod 64 above passage 52 is freely supported in a vertical groove 72 in the edge of wall 74 extending into well 50.

The cover 14 includes a monomer chamber lid 76 having a circumferential sealing gasket 78 for sealing against the top of the monomer well. Hollow mounting post 80 is integral with the lid and extends down from the lid into vertical passage 82 opening at the top of cover 14. Spring 84 is confined in the passage and extends from the bottom of the passage to the top of a recess in the bottom of post 80 to bias lid 76 upwardly. When the lid is open the spring 84 holds shoulder 86 at the top of post 80 against end 88 of crank arm 90. In this position, arcuate recess 92 at the end of the crank arm extends partially around the upper end of post 80 to lock the arm against rotation.

A shallow recess or dimple 94 in the top of lid 76 facilitates digital rotation and depression of the lid. Lip 96 extends around the lid and includes an inner bevel to facilitate aligning the lid with the top of the monomer chamber as the lid is lowered onto the chamber. The closed lid is located below crank arm 90 to free the arm for rotation.

Cover 14 includes a manual stirring drive 98 for rotating a bone cement cartridge and extension collar in chamber 20. The drive includes arm 90 and a drive shaft 100 mounted on arm 90 and extending down through cylindrical passage 101 from the top to the bottom of cover 14. Handle 102 is provided on the outer end of arm 90, away from shaft 100, to facilitate rotation of the arm and actuation of the drive. Drive gear 104, located on the bottom of the cover, is mounted on the lower end of shaft 100 and engages driven gear 106. Gear 106 is rotatably mounted on shaft 108 on the bottom of the cover. A drive disk 110 extends outwardly from the lower end of driven gear 106. Beveled alignment ring 112 extends around the lower side of disk 110, facing chamber 20 when the cover is mounted on the housing as in FIG. 2. A plurality of inwardly angled alignment ribs 114 are provided at intervals around ring 112 to facilitate centering the ring on the top of an extension collar of a bone cement cartridge positioned in chamber 20. A pair of diametrally opposed drive tabs 116 extend down from the outer edge of disk 110 outside ring 112 to engage external ribs on the extension collar and form a rotary connection between drive 98 and a cartridge in chamber 20.

Disk 110 is located between nozzle 54 and mixing chamber 20. Four kidney shaped openings 118 extend through disk 110 at spaced locations around the disk. If desired, the openings 118 may be in the form of radial notches extending in from the circumference of the disk. When handle 90 is locked in the position shown in FIGS. 2 and 10, with the handle extending away from the monomer well 50, an opening 118 is located below the nozzle 54 to permit a stream of monomer liquid from the nozzle to flow through the opening and into bone cement powder in a cartridge in chamber 20.

Post 91 extends a distance below lid 76. When the lid is positioned over the monomer chamber and lowered to the closed position shown in FIG. 11, the post engages upper end 64 of valve rod 62 to lower the rod and open valve 58. A concave—convex recess 93 is provided in the side of lid 76 above post 80. When the lid is lowered to close the top of the well recess 93 slides down along the adjacent end of the crank arm 90 and is aligned with the top of the well. The closed lid is below the crank arm so that the crank arm is unlocked for manual rotation. See FIGS. 10 and 11.

Figure 2:
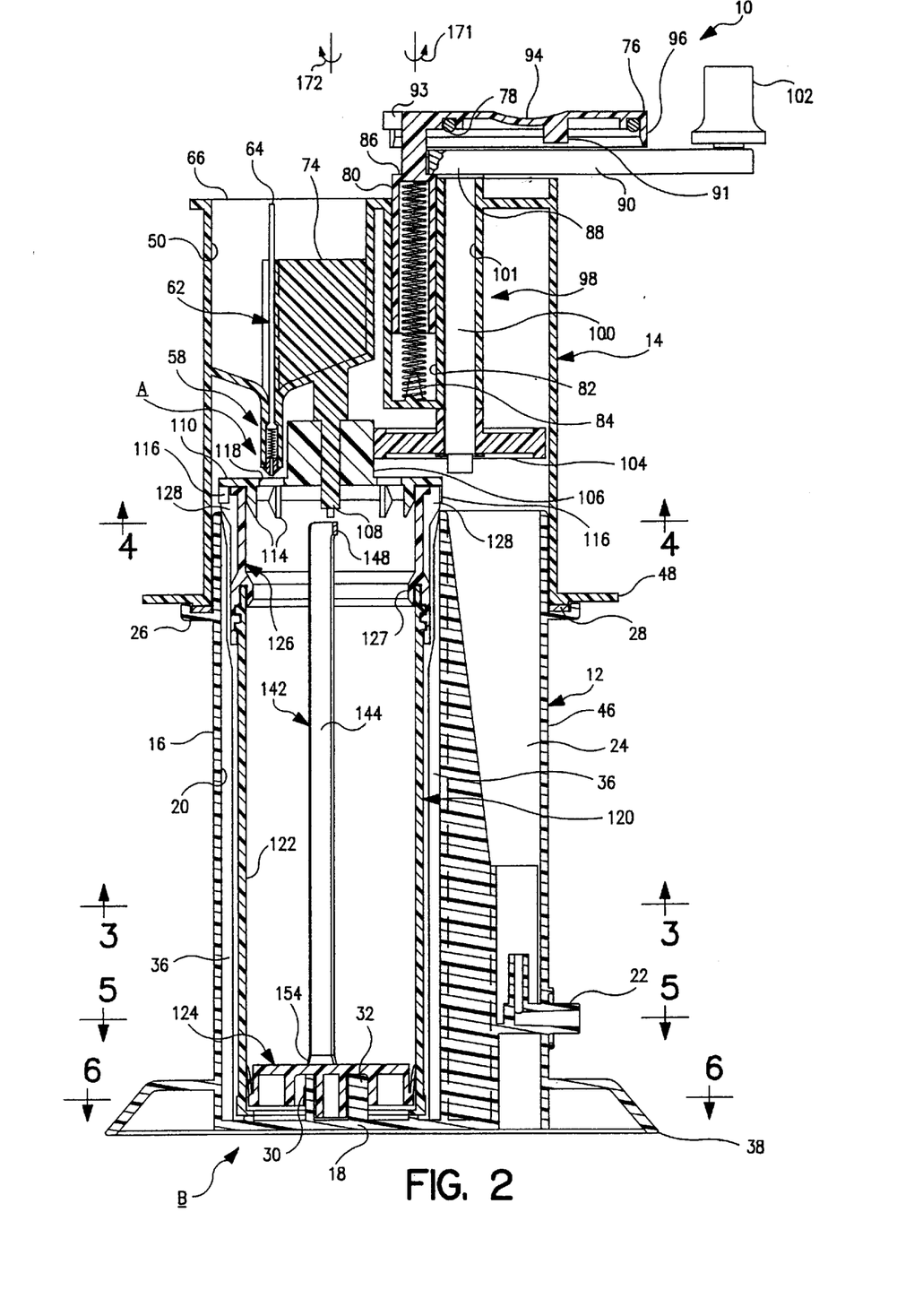
FIG. 2 is a vertical sectional view through the mixer shown in FIG. 1.
Figure 3:
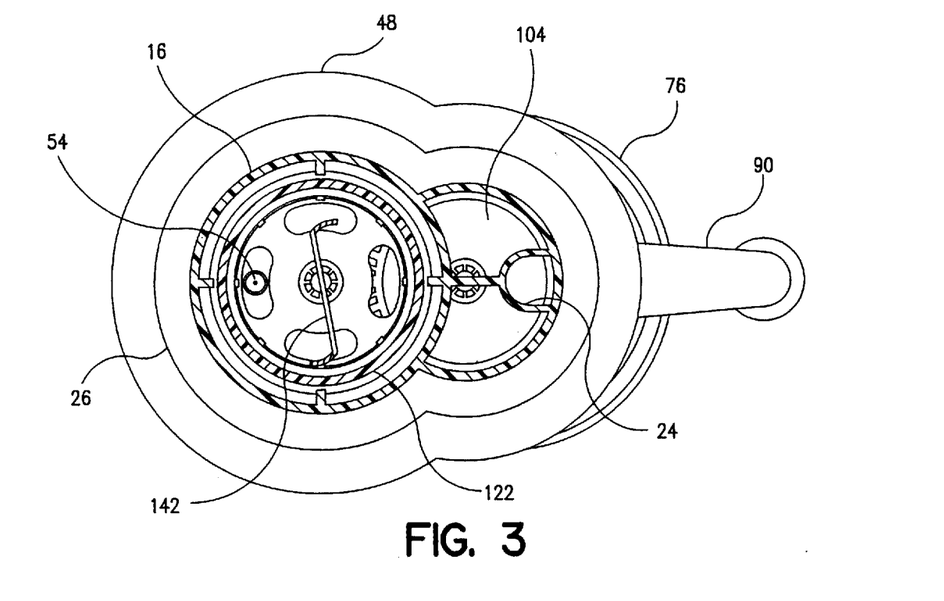
FIGS. 3 through 6 are sectional views taken along lines 3—3 through 6—6 of FIG. 2, respectively.
Figure 4:
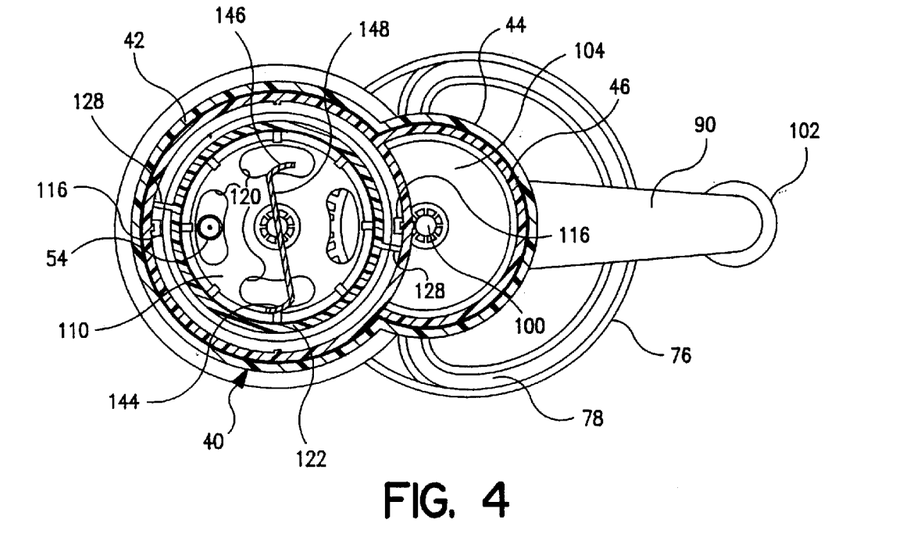
Figure 5:
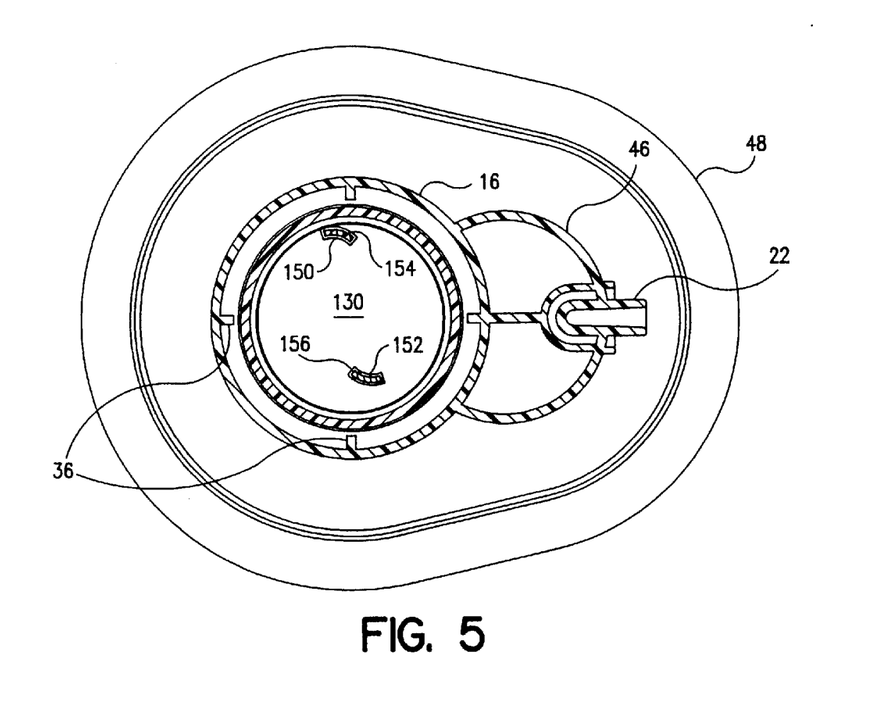
Figure 15:
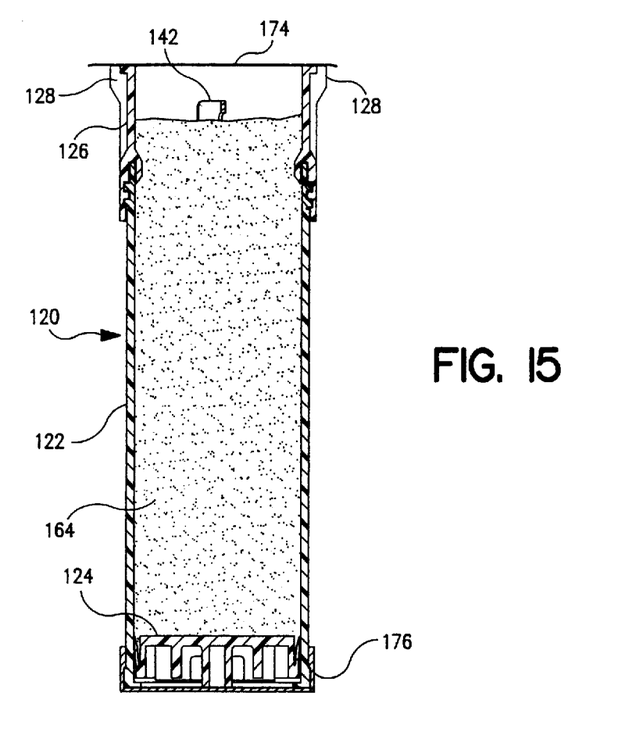
FIG. 15 is a sectional view of a pre-filled bone cement cartridge.

Bone cement mixer 10 mixes bone cement in a specialized bone cement cartridge 120 shown in FIG. 15. The cartridge 120 includes a plastic cylindrical body 122, piston 124 closing the lower end of the body, extension collar 126, stirrer 142 and a column of bone cement powder 164. Mounting threads are provided on the outer surface of the upper end of the body and threadably engage interior threads on collar 126 mounted on the upper end of body 122. As viewed from above, the collar is threaded onto the body by rotation in a clockwise direction. The collar includes an internal circumferential lip 127 which surrounds the top of body 122 and extends a short distance down into the interior of the body. Lip 127 guides powder into the cartridge and prevents leakage from the assembled body and collar. A pair of diametrally opposed external drive ribs 128 are provided on the top of collar 126, as shown in FIGS. 2 and 4.

Figure 9:
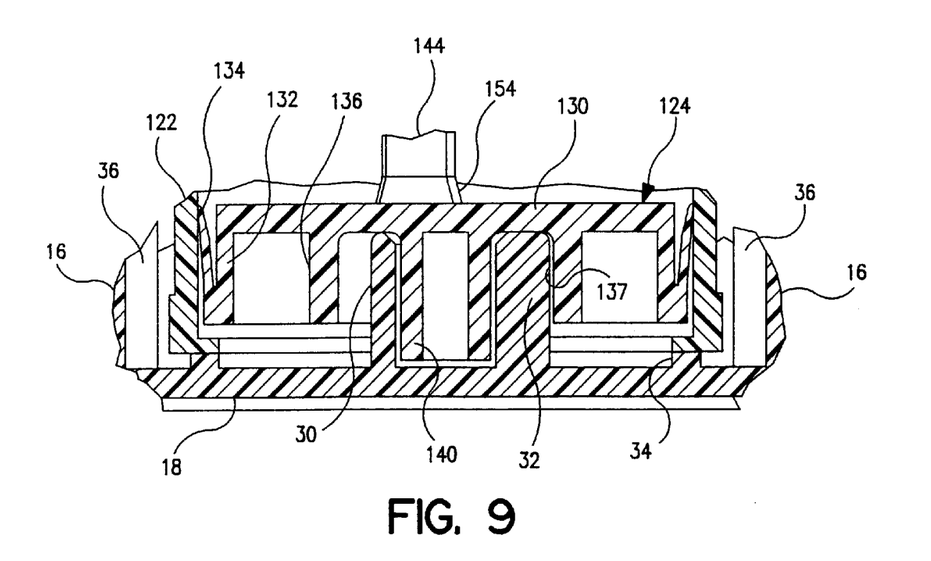
FIG. 9 is an enlarged view of portion B of FIG. 2.

Piston 124 includes a disk 130 facing the interior of body 122 and a cylindrical skirt 132 extending a short distance below the disk. The piston is preferably formed from molded thermoplastic resin. A cylindrical lip seal 134, integral with piston, extends around skirt 132 and is joined to the lower end of the skirt, as shown in FIG. 9. When the piston is fitted in body 122 the lip seal is biased radially outwardly against the body to prevent leakage from the cartridge. Integral strengthening wall 136, radial walls 138 and a central cylindrical plug 140 are formed on the lower surface of disk 130. When the bone cement cartridge is positioned in chamber 20 plug 140 fits in ring 30.

Figure 6:
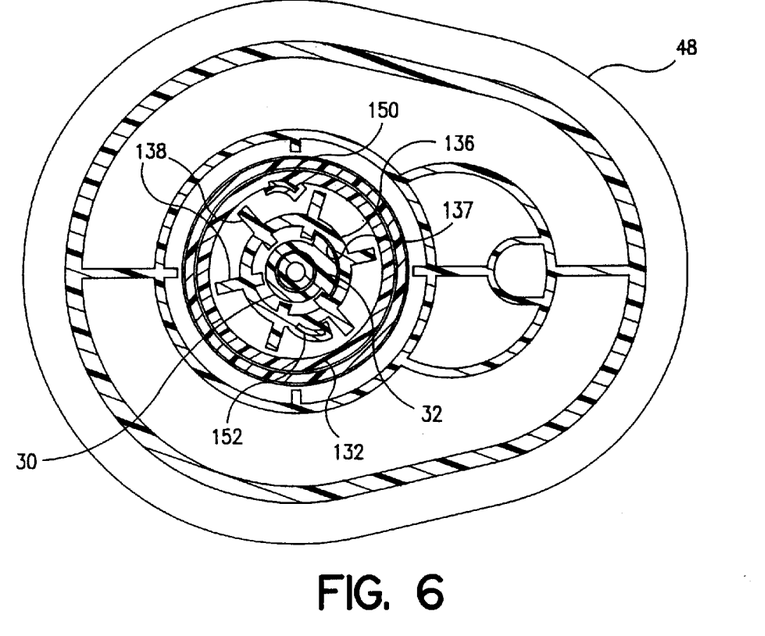

As shown in FIG. 6, the inner ends of all but one of the radial walls 138 extend inwardly beyond circular wall 136, providing an enlarged circumferential gap or keyway 137 inside wall 136 extending to either side of the foreshortened wall. When the cartridge, with piston in place, is inserted into chamber 20 alignment key 32 fits in the keyway 137 to orient the piston and U-shaped stirrer 142 mounted on the piston in a known circumferential position.

U-shaped stirrer 142 has two elongate, parallel and spaced apart mixing arms 144 and 146 and a bridge 148 joining the upper ends of the arms. The lower free ends of the arms extend through slots 150 and 152 in the piston. As shown in FIG. 4, arm 144 is located adjacent the inner wall of body 122 and arm 146 is located a distance further into the body than arm 144. The arms and slots are located off-center in the piston. Both arms extend along the length of the bone cement cartridge and into extension collar 126 a sufficient distance to assure the arms mix all of the bone cement powder in the cartridge and collar. The bridge is located in the collar above the powder 164. The stirrer is preferably stamped-formed from uniform thickness sheet strip metal stock. The arms have a uniform curved transverse cross section, as illustrated in FIG. 4, to facilitate mixing and movement of the piston along the arms.

Integral lip seals 154 and 156 project above the piston disk and surround the slots 150 and 152. The seals tightly engage the arms 144 and 146 to prevent material from leaking past the arms and out of the cartridge during bone cement mixing and extrusion of bone cement from the mixer. The piston slides freely and without leakage along arms 144 and 146 during extrusion of mixed bone cement from cartridge 120.

Bone cement is marketed by manufacturers in prepackaged amounts or doses which are mixed together by users to make a single dose of bone cement. Typically fine polymethyl methacrylate powder is packaged in forty gram doses and liquid methyl methacrylate monomer liquid is sealed in glass ampules in 20 milliliter doses. Mixer 10 may be used to mix one, two or three doses of bone cement powder and monomer liquid, depending upon the volume of cement required for a particular application.

Figures 11, 12:
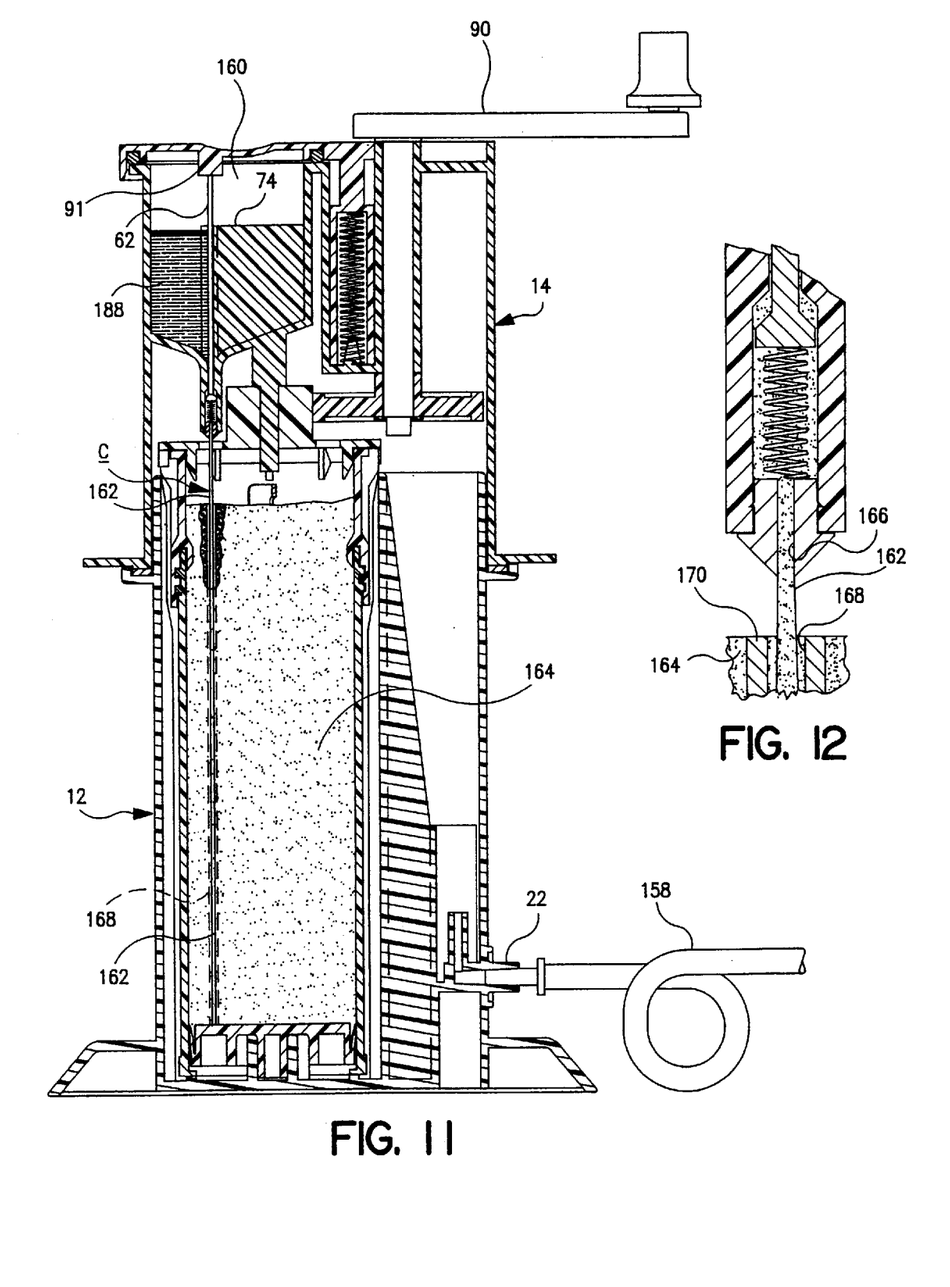
FIG. 11 is a vertical sectional view of the mixer illustrating discharge of monomer liquid into bone cement powder in a cartridge mounted in the mixer.
FIG. 12 is an enlarged view of portion C of FIG. 11.
Figure 13:
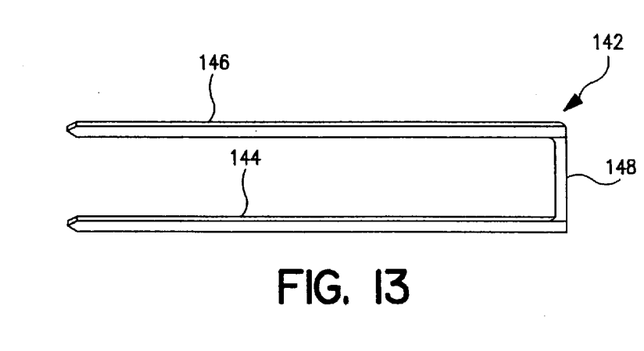
FIG. 13 is a side view of a stirrer.

Cartridge 120, with the piston, stirrer and collar in place, is filled with an appropriate member of doses of compacted bone cement powder prepared by a manufacturer and then sealed for shipment to a user. One, two or three doses of bone cement powder are placed into the cartridge. The bone cement powder may be either spherule and fragment type powder or spherule only type powder. FIG. 11 illustrates the level of a three dose column of bone cement powder 164 in the cartridge. After the cartridge has been filled with bone cement powder a seal 174 is applied to the upper end of the collar to confine the bone cement within the cartridge. The seal 174 may include a tab for use to remove the seal from the cartridge immediately prior to mixing the bone cement powder. The cartridge is sealed at atmospheric pressure. The seal is preferably permeable to assure that the interior of the cartridge is maintained at ambient pressure, despite changes in pressure. This feature is important because filled, sealed cartridges may be shipped from the manufacturing site to a user by air and exposed to reduced pressure during flight. A protective cap 176 is fitted over the lower end of the cartridge to protect the piston.

The operation of bone cement mixer 10 will now be described.

Prior to mixing bone cement, cover 14 is removed from housing 12. A bone cement cartridge loaded with an appropriate number of doses of bone cement is prepared for insertion into the mixer by removing the seal 174 at the top of the collar and removing the cap 176 covering the piston. The cartridge is held upright and is seated in chamber 20 as shown in FIG. 2. Ribs 36 guide the cartridge into place into chamber 20 and on base 38. With the piston keyway resting on the alignment key, the cartridge is rotated until the keyway and key are aligned permitting the cartridge to drop into position with the support ring 34 contacting the cartridge. In this way, the cartridge is properly seated in the housing without displacing the piston. The piston keyway 137 is now fitted around alignment key 32 and holds the piston and stirrer 142 in place so that they do not rotate with the cartridge body 122. The stirrer arms and bridge are held in fixed location away from nozzle 54 to permit an uninterrupted stream of monomer liquid to flow from the nozzle through disk 110 and into the powder in the cartridge.

After the cartridge is placed into the housing 12 cover 14 is fitted onto the housing. The lid and crank are locked in the position shown in FIGS. 2 and 7. Disk 110 is held against rotation with an opening 118 located below nozzle 54 and with drive tabs 116 short counterclockwise distances from ribs 128. The diameter of gear 106 is one half the diameter of gear 104, assuring that an opening 118 is properly located when handle 90 is locked in position extending away from the monomer well. Four openings 118 are disclosed in disk 110. In practice, only a single opening located below the nozzle need be provided.

Fitting of the cover on the housing moves the mounting disk 110 onto the top of the collar 126. This is facilitated by ribs 36 which hold the cartridge and collar in approximate alignment with disk 110. Beveled ring 112 is seated a short distance into the collar. The members 114 guide the ring into the collar.

With the cover in place flange 48 engages gasket 28 and the interior of mixing chamber 20 is sealed closed. Port 22 is then connected to a vacuum source through a tube 158 to evacuate the mixing chamber and remove entrapped air from the bone cement powder. During evacuation of the mixer, the appropriate number of doses of monomer liquid for mixing with the bone cement powder in the cartridge are poured into open monomer well 50. Spring 70 holds valve 58 closed to prevent monomer liquid from flowing into the mixer.

Figure 7:
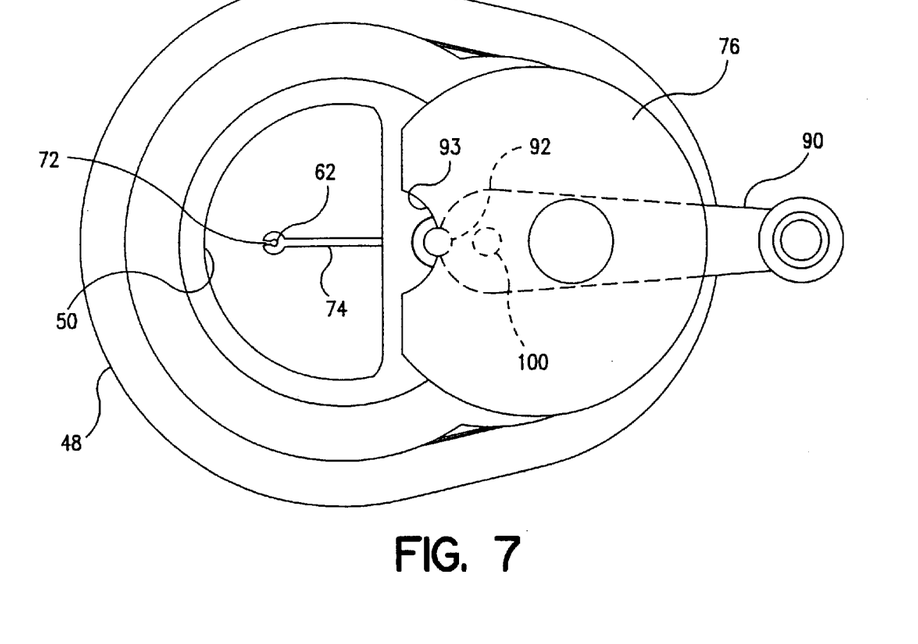
FIG. 7 is a top view of the mixer shown in FIG. 1.
Figure 10:
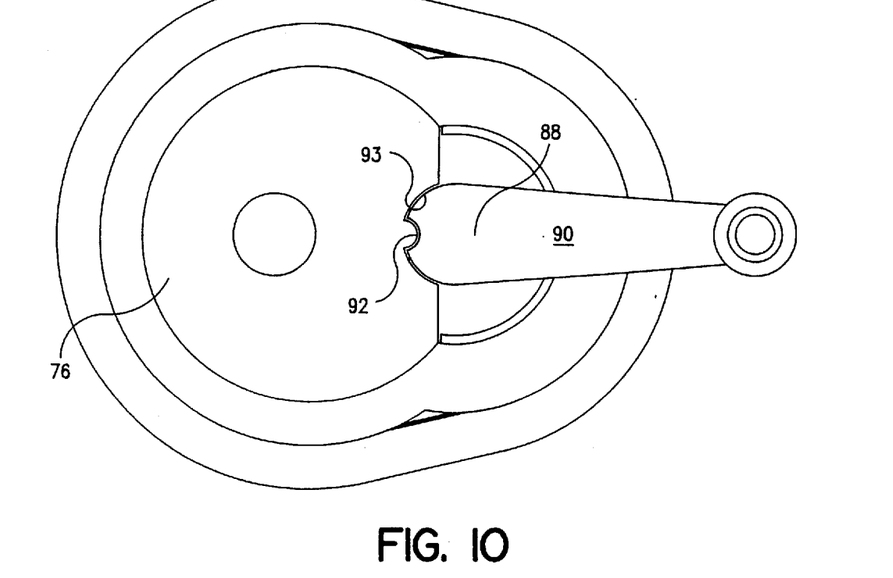
FIG. 10 is a top view of the mixer with the monomer chamber lid closed.

Following reduction of the pressure in the mixer by about 12 pounds per square inch (PSI), the lid 76 is rotated 180 degrees from the position of FIG. 7 to the position of FIG. 10, either by gripping the edges of the lid or by digitally engaging dimple 94. The lid is then depressed to the position of FIG. 11 where gasket 78 engages the top of the monomer well and closes off the top of the well. Post 91 engages and lowers the valve rod 62 to open valve 58. Closing of the lid captures a volume of air at atmospheric pressure in space 160 at the top of the well, above the monomer in the well and prevents escape of monomer liquid vapor.

When the valve 58 is opened, the pressure drop across the nozzle, essentially −12 PSI, rapidly flows monomer liquid down passage 52 and out the flow passage 166 in nozzle 54 in a small diameter, high velocity stream 162. The stream has a fixed vertical orientation during delivery of liquid monomer into bone cement in the cartridge. The orientation of the stream is determined by the fixed vertical orientation of nozzle 54. The vertical stream 162 flows through aligned opening 118 in disk 110 and down into the evacuated bone cement column 164 in the cartridge and extension collar. The diameter of the monomer stream 162 above the powder diverges only slightly from the diameter of the passage in the nozzle. See FIGS. 11 and 12. The monomer stream penetrates the height of the bone cement column and is absorbed into the bone cement powder in the column. Bone cement liquid does not puddle on the top of the bone cement powder. Monomer liquid is absorbed into the bone cement powder relatively uniformly along the height of the column. Uniform distribution of monomer liquid along the column facilitates mixing of the monomer liquid into the bone cement powder. During mixing there is no need to displace monomer liquid vertically to make uniform bone cement. The person operating mixer 10 can observe the level of monomer liquid in well 50 through the transparent side wall of the cover 14 and determine when all monomer liquid has been flowed into the cement powder.

The leading end of the monomer stream 162 hits the bone cement powder in column 164 and is absorbed into the powder. The wetted powder shrinks laterally away from the monomer stream to form a cylindrical passage or well 168 surrounding the stream and having a diameter greater than the stream. The well extends along the length of the stream. A cylinder 170 of wetted bone cement powder-rich in monomer liquid surrounds passage 168. The powder in the column away from the cylinder remains dry. The powder dissolves into the monomer liquid as monomer liquid wicks outwardly into the surrounding evacuated and dry powder.

After all monomer liquid has been flowed into the bone cement powder the air captured in the well when the lid was closed is evacuated from the mixer through port 22. The lid is held closed against spring 70 by the negative pressure in the mixer and continues to hold valve 58 open. The air from well 50 bypasses the mixture and does not form inclusions in the cement. Lid 76 is held closed during mixing until the pressure in the mixing chamber is returned to atmospheric pressure prior to removal of the cover 14 from housing 12. Spring 70 then opens the lid.

FIG. 11 illustrates distribution of a three dose volume of monomer liquid from the monomer well into a 7 inch tall and 1¹¹⁄₁₆ inch diameter column of three doses of bone cement powder. Mixer 10 may also be used for distributing monomer liquid along two dose and one dose columns of bone cement powder preloaded in cartridges, as described. If desired, bone cement powder may be manually poured into an open cartridge using a funnel. Fluffed powder in the cartridge is compacted by tapping or vibration.

In mixing one or two doses of cement, slightly more monomer liquid may be distributed initially to the lower portion of the column than to the upper portion. During mixing the monomer distribution equalizes along the vertical extent of the mixture.

After monomer liquid is flowed into the bone cement powder, mixing is initiated by rotating crank 90 in a counterclockwise direction indicated by arrow 171, as viewed from the top of the mixer, to rotate disk 110 in a clockwise direction as indicated by arrow 172. Rotation of the disk moves drive tabs 116 into contact with drive ribs 128 on collar 126 to rotate the collar and threadably attached body 122 in the clockwise direction. Rotation of the collar tightens the threaded connection between the collar and the body to assure that the collar and body rotate together. Piston 124 is held against rotation on bottom wall 18 by key 32 seated in keyway 137. Stirrer 142 is likewise held stationarily with the lower ends of arms 144 extending into slots 150 and 152 in the held piston. During mixing the volume of the powder and liquid shrinks and all the mixed cement is held in body 122. Mixing takes about 45 seconds.

Rotation of the collar and body move the bone cement powder and monomer liquid in the bone cement powder around the stationary stirring arms 144 and 146 to mix the cement. Arm 144 is located radially outwardly of arm 146 and most efficiently mixes the bone cement powder located in the outside of column 164. Arm 146 is located closer to the center of the column and most efficiently mixes the bone cement powder located near the center of the column. Both arms have vertical surfaces and a uniform curved transverse cross section. The uniform cross section and vertical surfaces allow the piston to move along the arms of the stirrer when cement is extruded from the cartridge.

Figure 14:
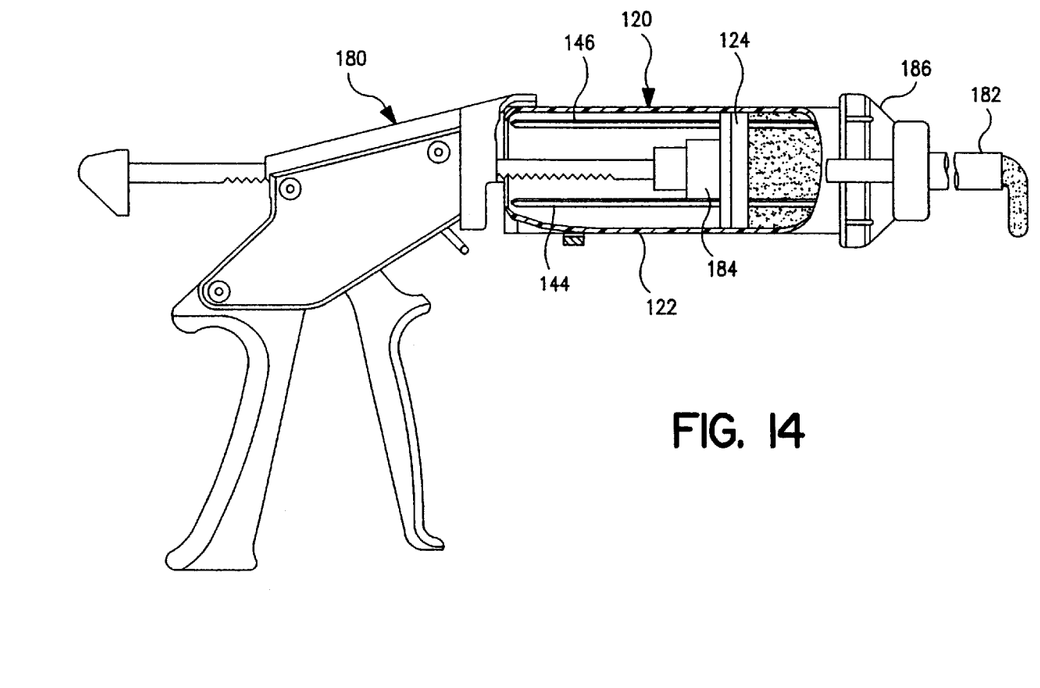
FIG. 14 is a view, partially broken away, of a bone cement gun dispensing mixed bone cement from a bone cement cartridge.

After mixing has been completed the mixer is disconnected from the vacuum source and cover 14 is removed from housing 12. The upper end of collar 26 is gripped and the cartridge removed from the mixer. The collar is then unthreaded from cartridge body 122 and a nozzle 182 with threaded hub 186 is screwed on in its place. The cartridge is loaded into a conventional bone cement gun 180. Gun 180 includes a drive member 184 which engages the exposed end. of cartridge piston 124. Gun 180 is actuated to move member 184 against piston 124, slide the piston along the cartridge body 122 and extrude mixed bone cement from nozzle 182. During extrusion of the mixed bone cement, the piston 124 moves freely along the mixer arms 144 and 146. Lip seals 154 on the piston prevent leakage of bone cement through the piston as the piston moves along the arms. Likewise, lip seal 134 prevents leakage of mixed bone cement between the piston and the body 122. The bridge end of stirrer 142 is moved against the hub 186 of nozzle 182. The stirrer does not interfere with extrusion of the mixed bone cement from the gun.

During flowing of monomer liquid into the bone cement powder the monomer stream 162 flows at a speed dependent upon the pressure differential between space 160 and the evacuated interior of the mixer. In one test three doses of monomer liquid were placed in the monomer well leaving an air space at the top of the closed well equal to about ⅔ the volume of monomer liquid in the well. The interior of the mixer was evacuated to about 12 PSI below atmospheric pressure. The lid was closed, the valve at the bottom of the monomer well was opened and the 12 PSI pressure differential flowed monomer liquid from the well through a nozzle in a high speed stream which penetrated a 7 inch high three dose column of bone cement in the cartridge and sleeve.

As monomer liquid is flowed from the well the size of the air space 160 grows and the pressure differential between the well and the interior of the mixer decreases. Just before all of the monomer liquid is flowed into the mixer the size of the air space has doubled, reducing the pressure differential to about 4.7 PSI. Despite the reduction in pressure differential, the monomer liquid is injected into the column at a sufficient speed to penetrate the column and is distributed along the height of the column.

In the foregoing test, three doses of monomer liquid (sixty ml. of methyl methacrylate) was flowed through a nozzle having an interior diameter of 0.066 inch in about 8 seconds at an average calculated speed of about 4.3 feet per second. The monomer liquid was very rapidly flowed into the bone cement. The bone cement was then subsequently mixed, as described above, with the resultant cement having a slightly greater viscosity at the bottom of the cartridge than at the top of the cartridge. The flow passage in the nozzle had a cross sectional area of 0.0034 in$^2$.

Another test was conducted like the foregoing test with the exception that the diameter of the nozzle flow passage was reduced to 0.022 inch with a cross sectional area of 0.00038 in$^2$. The monomer liquid was flowed in a high velocity stream into a 7 inch column of bone cement powder and was distributed essentially uniformly along the height of the column. All of the monomer liquid was dispensed in about 24 seconds at a calculated average speed of about 10 feet per second. Compared to cement mixed using the 0.066 inch nozzle, the distribution of the monomer liquid along the column was improved and the viscosity of the mixed cement was more uniform, although the time for flowing monomer liquid into the column was increased.

The foregoing tests used nozzles with cross sectional flow areas of 0.0034 in$^2$ and 0.00038 in$^2$. Clearly, nozzles having cross sectional areas between the areas of the two tested nozzles may be used. Likewise, the stream may be flowed into the bone cement powder at speeds between 4.3 feet per second and 10 feet per second. Also, a pressure differential different than −12 PSI may be used to form the high speed narrow stream of bone cement liquid. Nozzles larger or smaller than the tested nozzle may be used and the bone cement liquid may be flowed into the cement powder in higher or lower speed streams.

The viscosity of bone cement mixed as described above was tested by extruding all mixed bone cement in a cartridge as a long cylinder of cement on a support surface. The viscosity of the bone cement was observed along the length of the cylinder by noting the change of shape or sag of the bone cement. The cement was mixed after the pressure in the interior of the mixer was reduced 12 PSI below atmospheric pressure, using a monomer nozzle having an interior diameter of 0.066 inch. The cement was mixed for about 45 seconds. Bone cement mixed from three doses of bone cement powder and three doses of monomer liquid had slightly less sag at the bottom (piston) end. Bone cement mixed from one or two doses of powder and monomer liquid had essentially uniform sag along its length and uniform viscosity. However, the differences in viscosity of these cements were not significant.

The foregoing tests were conducted using Simplex P Radiopaque bone cement powder and monomer liquid manufactured by How medica Inc. of New Jersey.

Bone cement mixer 10 dispenses monomer liquid from a monomer chamber or well through a nozzle to form a narrow high speed stream of monomer liquid that penetrates a column of evacuated bone cement powder. A lid is provided to close off the top of the monomer chamber and actuate a valve to initiate flow of monomer liquid through the nozzle. However, the mixer need not include a lid for the monomer chamber or a valve for controlling flow of monomer liquid from the monomer chamber into the interior of the mixer and the column of bone cement powder.

Monomer liquid may be flowed in a narrow high speed stream into a bone cement column using a mixer as disclosed without a lid and without a valve in discharge passage 52 leading from the monomer chamber to the nozzle. In this case, operation of the mixer would be as described previously with the exception that during evacuation of the interior of the mixer air would flow through the open monomer chamber and nozzle into the interior of the mixer and be withdrawn through the vacuum port. The vacuum source reduces the pressure in the mixing chamber despite the limited flow of air through the nozzle. After the vacuum source reduces the pressure of the interior of the bone cement mixer the operator places the proper number of doses of monomer liquid into the monomer chamber. The pressure differential between the monomer liquid in the monomer chamber at atmospheric pressure and the reduced pressure interior of the mixer forms a narrow high speed stream of monomer liquid which penetrates the column of bone cement in the cartridge located below the nozzle. The operator can observe flow of monomer liquid from the well. When all liquid has been dispensed into the bone cement powder the bone cement can be manually mixed as previously described. The interior of the mixer is maintained under vacuum during mixing. Air drawn into the chamber through the nozzle is evacuated and does not interfere with mixing and does not form inclusions in the mixed cement. After mixing is completed, the vacuum source is disconnected from the mixer, the cover is removed and the cartridge and collar are removed from the housing for extrusion, again as previously described.

Bone cement mixer 10 may be used for mixing bone cement without a lid for the monomer chamber but with a valve located in discharge passage 52. When using this mixer, mixing proceeds as previously described. An appropriate number of doses of monomer liquid is poured into the monomer chamber and the valve is opened at the appropriate time to release monomer liquid for flow through the nozzle in a high speed narrow stream and penetration into the bone cement column. After the monomer has been flowed into the bone cement powder the valve is preferably closed. The bone cement is then mixed. The valve may be left open during mixing if desired.

Bone cement mixer 10 may also be used for mixing bone cement with a lid for the monomer chamber but without a valve in the discharge passage. When using this mixer, mixing proceeds as previously described with the exception that the lid on the monomer well is closed during initial evacuation of the interior of the mixer. After evacuation, lid is opened and an appropriate quantity of monomer liquid is poured into the monomer chamber. The lid is closed on the chamber as monomer liquid in the chamber is flowed out through the nozzle in a high speed narrow stream and penetrates the column of bone cement powder. The bone cement is then mixed. Preferably, the lid is reapplied to the top of the monomer chamber immediately after monomer liquid is poured into the well, in order to reduce escape of monomer liquid vapor and flow of air into the mixing chamber.

In mixer 10 the stream of bone cement liquid is flowed vertically down into the column of bone cement powder. Nozzle 54 is located a distance above the top of the column so that the stream flows a distance through the evacuated mixing chamber before it contacts the top of the bone cement column.

The stream need not be directed vertically down into the bone cement column. The stream may be flowed into the bone cement from any direction. However, the stream should be flowed essentially in the direction of the long axis of the bone cement powder. The liquid in the stream is distributed essentially uniformly along the flow path in the cement powder as described.

Additionally, the nozzle need not be located a distance from the cement powder into which the liquid stream is flowed. The nozzle may be positioned at or even in contact with the powder.

The narrow stream must be flowed into the powder at a high speed in order to penetrate the powder and permit absorption of the liquid as described. Cement liquid which is gravity poured onto bone cement powder will not penetrate the powder. Gravity poured liquid does not move at a sufficiently high velocity.

The maximum and minimum diameters for the penetrating stream and the maximum and minimum speeds for the penetrating stream vary depending upon the particular application. A stream having a given diameter penetrates bone cement powder better at a higher speed. Also, the greater the speed of a stream and the smaller size of the stream, the more likely that the stream reaches the bottom of the mixing chamber. The information given concerning the size of nozzle flow apertures, the speed at which liquid streams are flowed into bone cement powder, the pressure drop at the nozzle and the duration for flowing all cement liquid into bone cement powder stated above are exemplary and are not meant to limit the invention. In any event, this information relates to mixing How medica Simplex P bone cement powder and liquid only and may not be correct for other bone cements.

The stream of monomer liquid flowed from nozzle 54 into and through bone cement powder column 164 is caused by an approximate −12 PSI pressure differential across the nozzle 54. In disclosed mixer 10 the pressure differential is created by a pressure differential generator, a conventional vacuum source or pump connected to the end of tube 158 away from port 22. Any type of vacuum pump may be used.

Other types of pressure differential generators are contemplated. The generator may lower the pressure in the mixing chamber below atmospheric pressure to provide the required pressure differential by expanding the volume of the mixing chamber without withdrawing air from the mixing chamber. This may be done by mounting a large diameter piston pump on the mixing chamber and then withdrawing the piston along the barrel of the pump to reduce the pressure in the chamber. Alternatively, a flexible chamber wall may be provided together with a puller to move the wall away from the mixer and reduce the pressure in the chamber.

Alternatively, the pressure differential generator may increase the pressure of the cement liquid to be flowed through the nozzle. A pump may be provided to pressurize and flow cement liquid to the nozzle. The liquid may be pressurized by the piston of a syringe or by pressurized gas to generate the pressure differential. Alternatively, the liquid could be confined within a closed pressure generator chamber having a flexible wall. Inward collapse of the wall would reduce the volume of the chamber, pressurize the liquid and flow liquid through the nozzle with the required pressure differential to generate the stream.

While I have illustrated and described a preferred embodiment of my invention, it is understood that this is capable of modification, and I therefore do not wish to be limited to the precise details set forth, but desire to avail myself of such changes and alterations as fall within the purview of the following claims.

What I claim as my invention is:

1. A device for stirring and then extruding liquid bone cement, the device comprising:
   a) a cylindrical body having opposed ends and a hollow interior between the ends;
   b) a cylindrical piston positioned in one end of the body to close the end of the body while permitting relative rotation between the piston and the body and movement of the piston along the body, the piston including an off-center stirrer arm opening; and
   c) a stirrer in the body, the stirrer including an elongate arm having a first portion in the opening in the piston and a second portion extending away from the piston and along the interior of the body, wherein relative rotation of i) the body and ii) the piston and the stirrer stirs bone cement powder and bone cement liquid in the body to form liquid bone cement, and movement of the piston along the interior of the body extrudes liquid bone cement from the other end of the body and moves the piston along the length of the stirrer arm.

2. The device as in claim 1 wherein the piston includes a first seal extending around the opening and engaging the exterior of the arm.

3. The device as in claim 2 wherein the piston includes a second seal extending around the piston and engaging the interior of the body.

4. The device as in claim 1 wherein the stirrer arm is formed from uniform thickness material and has a uniform transverse cross section; and said stirrer arm opening comprises a slot.

5. The device as in claim 4 wherein said arm is curved in transverse cross section and the slot is curved.

6. The device as in claim 1 wherein said cylindrical body includes a cylindrical cartridge and an annular member removably mounted on the cartridge, said piston located in the cartridge away from the annular member, said stirrer extending from the piston into the annular member.

7. The device as in claim 6 including a quantity of bone cement powder in the cylindrical body.

8. The device as in claim 7 wherein said bone cement powder completely fills the cartridge and extends into the annular member.

9. The device as in claim 8 wherein the annular member comprises a collar, and including a seal closing the end of collar away from the piston.

10. The device as in claim 9 wherein said seal is permeable.

11. The device as in claim 9 including a closure closing the end of the cartridge adjacent to the piston.

12. The device as in claim 1 wherein said stirrer includes a second arm extending parallel to and spaced from said first arm and a bridge joining said arms; and said piston includes a second stirrer arm opening, the second arm extending into the second stirrer arm opening.

13. The device as in claims 12 wherein the bridge joins the ends of the arms away from the piston and the stirrer is U-shaped.

14. The device as in claim 12 wherein piston includes a pair of first seals, each first seal extending around one stirrer arm opening and engaging a stirrer arm, and a second seal extending around the circumference of the piston and engaging the cylindrical body.

15. The device as in claim 12 wherein one stirrer arm is located closer to the cylindrical body than the other stirrer arm.

16. The device as in claim 12 wherein said mixing arms are curved in transverse cross section; and said slots are curved and conform in shape to the transverse cross sections of the mixing arms.

17. The device as in claim 12 including a quantity of dry bone cement powder in the interior of the cylindrical body, and a seal closing the end of the body away from the piston.

18. The device as in claim 17 wherein said seal is permeable.

19. The device as in claim 17 wherein the body includes a cylindrical cartridge and an annular member mounted on the cartridge.

20. The device as in claim 19 wherein said annular member comprises a cylindrical collar.

21. The device as in claim 1 wherein the piston includes a cylindrical skirt and a circumferential lip seal overlying the skirt, the lip seal engaging the body.

22. The device as in claim 1 including a first surface rotatable with the body and a second surface rotatable with the piston and stirrer, wherein rotation of one surface relative to the other surface relatively rotates the body and stirrer.

23. The device as in claim 1 wherein the stirrer arm opening in the piston has a non-circular transverse cross section, and the stirrer arm has a non-circular cross section conforming to the cross section of the stirrer arm opening so that the stirrer arm cannot rotate in the piston.

24. A package for stirring and extruding bone cement, the package comprising a hollow cylindrical body having opposed ends, a cylindrical piston fitted in one end of the body for rotation relative to the body and movement along the interior of the body, a first stirrer opening extending through the piston inwardly from the body, said first stirrer opening having a non-circular transverse cross section, a stirrer including a elongate stirring arm having a uniform transverse cross section conforming to the shape of the stirrer opening in the piston, said stirrer arm extending into the stirrer opening and away from the piston along the interior of the body; a body of dry bone cement powder substantially filling the interior of the body, said stirring arm extending along the body of bone cement powder; and a removable first seal closing the end of the body away from the piston, wherein relative rotation of the body and stirrer piston stirs the bone cement powder with bone cement liquid placed in the body and movement of the piston along the body and the stirrer extrudes stirred bone cement from the other end of the body.

25. The package as in claim 24 wherein said body includes a cylindrical cartridge and an annular member removably mounted on one end of the cartridge, said piston located in the other end of the cartridge away from the annular member, said first seal closing the end of the annular member away from the cartridge.

26. The package is in claim 25 wherein the annular member comprises a cylindrical collar.

27. The package as in claim 25 wherein said first seal is permeable.

28. The package as in claim 25 including a closure covering the end of the cylindrical cartridge adjacent the piston.

29. The package as in claim 25 wherein said stirrer includes a second stirring arm, said stirring arms are straight and parallel each other, said piston includes a second stirrer opening, and said second stirring arm extends into said second opening.

30. The package as in claim 29 wherein said stirrer is U-shaped and includes a bridge joining the first and second stirring arms, said bridge located away from the piston.

31. The package as in claim 30 wherein said stirring arms are formed from uniform thickness metal and are curved in transverse cross section.

32. The package as in claim 31 wherein one stirring arm is located closer to the body than the other stirring arm.

33. The package as in claim 24 wherein the first stirrer opening is located to one side of the center of the piston.

34. A device for stirring and then extruding liquid bone cement, the device comprising:

a) a cylindrical body having opposed ends and a hollow interior between the ends;

b) a cylindrical piston positioned in one end of the body to close the end of the body while permitting relative rotation between the piston and the body and movement of the piston along the body, the piston including a stirrer arm opening having a non-circular transverse cross section; and c) a stirrer in the body, the stirrer including an elongate arm having a first portion in the opening in the piston and a second portion extending away from the piston and along the interior of the body, the stirrer arm having an uniform, non-circular cross section conforming to the cross section of the stirrer arm opening so that engagement between the first portion of the stirrer arm and the piston prevents relative rotation of the stirrer arm and piston, wherein relative rotation of i) the body and ii) the piston and the stirrer stirs bone cement powder and bone cement liquid in the body to form liquid bone cement, and movement of the piston along the interior of the body extrudes liquid bone cement from the other end of the body and moves the piston along the length of the stirrer arm.

* * * * *